United States Patent [19]

Cuprak

[11] Patent Number: 5,078,692
[45] Date of Patent: Jan. 7, 1992

[54] ARTICLE GRIPPING DEVICE

[76] Inventor: Raynette M. Cuprak, 273 E. 30th St., Yuma, Ariz. 85364

[21] Appl. No.: 391,994

[22] Filed: Aug. 10, 1989

[51] Int. Cl.⁵ ............................................. A61M 5/32
[52] U.S. Cl. ..................................... 604/192; 604/263
[58] Field of Search ............... 604/192, 197, 198, 263, 604/106

[56] References Cited

U.S. PATENT DOCUMENTS

| | | | |
|---|---|---|---|
| 4,559,042 | 12/1985 | Votel | 604/192 |
| 4,737,149 | 4/1988 | Gillilan | 604/192 |
| 4,767,412 | 8/1988 | Hymanson | 604/192 |
| 4,781,697 | 11/1988 | Slaughter | 604/192 |
| 4,880,413 | 11/1989 | Giuffre et al. | 604/192 |
| 4,900,309 | 2/1990 | Netherton et al. | 604/263 X |
| 4,973,315 | 11/1990 | Sincock | 604/192 |

*Primary Examiner*—C. Fred Rosenbaum
*Assistant Examiner*—Corrine Maglione
*Attorney, Agent, or Firm*—Fleit, Jacobson, Cohn, Price, Holman & Stern

[57] ABSTRACT

A device for gripping, holding or stabilizing an article, object or item and more particularly an article gripping device in the form of an annular member adapted to encircle and receive the article to be gripped with the annular member including a hollow or tubular stem which tapers to a graduated or stepped smaller tubular end or lumen toward the bottom with a flexible, resilient, spiral tail extending from the bottom end to facilitate various sized articles, objects or items being held by the non-dominant hand while performing certain work functions with the dominant hand thereby inadvertently protecting the non-dominant hand while performing such work functions with the dominant hand. The gripping device is of one-piece construction from flexible, resilient, rubber or plastic material and in one embodiment includes a longitudinal slit extending from top to bottom to enable the gripping device to be opened and laterally receive or be placed on an article to be held or gripped with other embodiments of the invention including a peripherally continuous annular member and stem into which articles to be held or gripped can be inserted.

8 Claims, 1 Drawing Sheet

U.S. Patent
Jan. 7, 1992
5,078,692
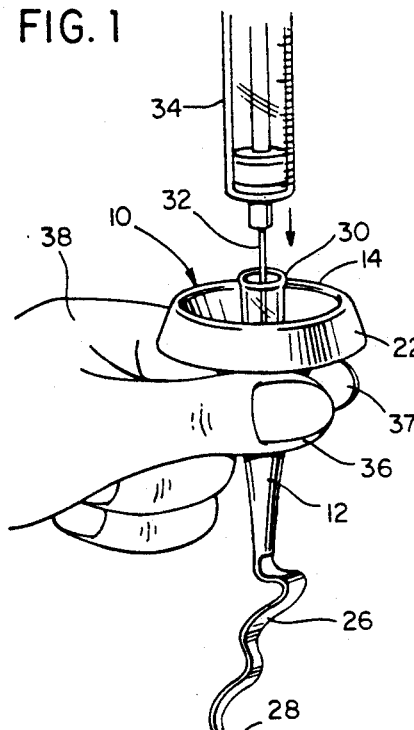
FIG. 1
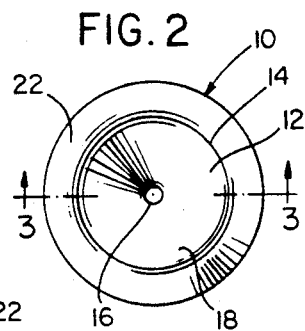
FIG. 2
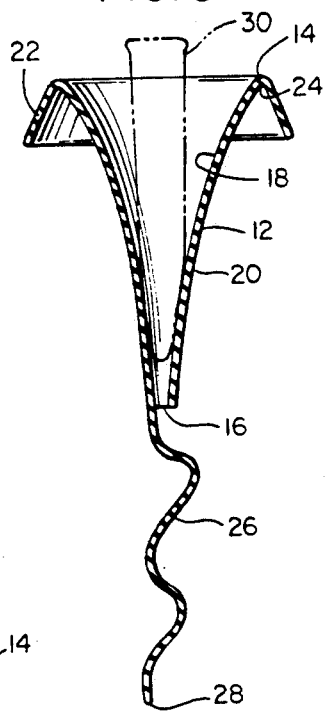
FIG. 3
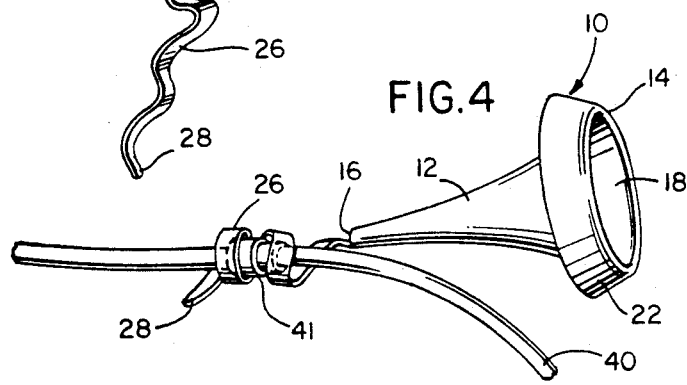
FIG. 4
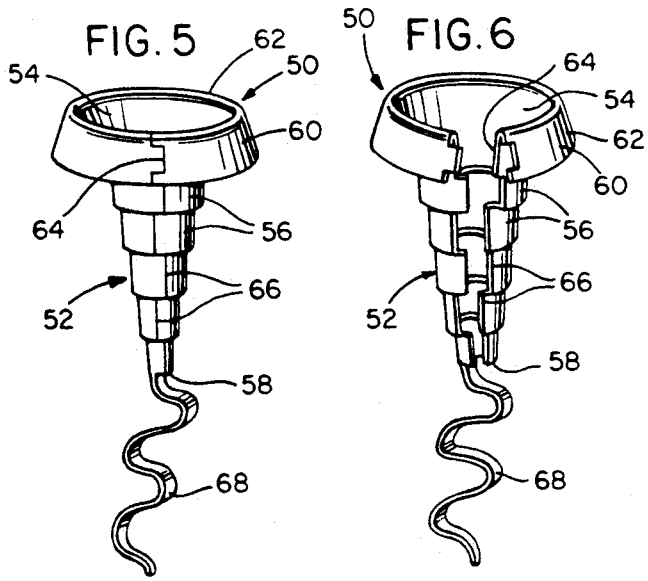
FIG. 5
FIG. 6
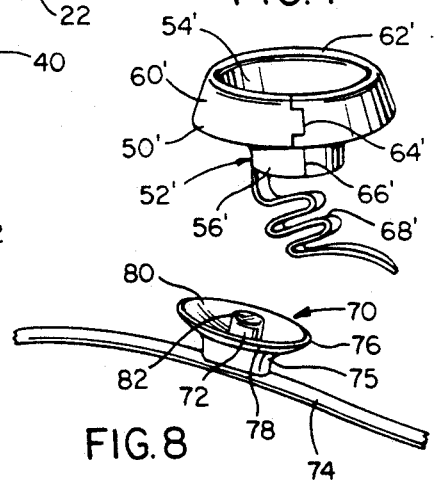
FIG. 7
FIG. 8

ARTICLE GRIPPING DEVICE

BACKGROUND OF THE INVENTION

1. Field of the Invention

The present invention generally relates to a device for gripping, holding or stabilizing an article, object or item and more particularly an article gripping device in the form of an annular member adapted to encircle and receive the article to be gripped with the annular member including a hollow or tubular stem which tapers to a graduated or stepped smaller tubular end or lumen toward the bottom with a flexible, resilient, spiral tail extending from the bottom end to facilitate various sized articles, objects or items being held by the non-dominant hand while performing certain work functions with the dominant hand thereby protecting the non-dominant hand while performing such work functions with the dominant hand. The gripping device is of one-piece construction from flexible, resilient, rubber or plastic material and in one embodiment includes a longitudinal slit extending from top to bottom to enable the gripping device to be opened and laterally receive or be placed on an article to be held or gripped with other embodiments of the invention including a peripherally continuous annular member and stem into which articles to be held or gripped can be inserted. A major use area of the invention includes but is not limited to use in the medical field in which needle sheaths, IV tube ports, medicament vials, ampules and the like are held by the non-dominant hand while the dominant hand holds a syringe or the like and inserts the needle with the gripping device protecting the non-dominant hand from accidental break in skin integrity caused by accidental needle puncture or needlestick.

2. Information Disclosure Statement

The following U.S. Pat. Nos. relate to syringe needle sheaths or caps having a finger protecting shield associated therewith.

4,737,149
4,740,204
4,767,412
4,781,697
4,799,927

None of the above listed patents disclose the specific structure of the article gripping device of this invention.

SUMMARY OF THE INVENTION

An object of the present invention is to provide an article gripping device which will protect the fingers of the hand that holds or grips the device while a work operation is being performed on the article, object or item being held.

Another object of the invention is to provide an article holding device in accordance with the preceding object which includes a tubular annular member having a depending tubular stem into which an article, object or item to be held can be inserted with the lower end of the stem including a flexible, resilient tail which can be wrapped partially or totally around the article, object or item to enable effective gripping and holding of articles, objects or items having wide variations in size, configurations and limitations as to forces exerted thereon.

A further object of the invention is to provide an article gripping device in accordance with the preceding objects which in one embodiment includes an annular member which is peripherally continuous and in another embodiment includes an annular member having a longitudinal slit or access opening in one side to enable the annular member and stem to be pivoted to an open position to enable lateral insertion of or lateral insertion onto an article, object or item to be gripped or held.

Still another object of the invention is to provide an article gripping device which is simple in construction, capable of many effective uses and relatively inexpensive to manufacture while effectively and safely holding articles of various shapes and sizes.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the article gripping device of the present invention illustrating one use thereof.

FIG. 2 is a top plan view of the article holding device illustrated in FIG. 1.

FIG. 3 is a vertical, sectional view taken substantially upon a plane passing along section line 3—3 on FIG. 2 illustrating further specific structural details of this embodiment of this invention.

FIG. 4 is a perspective view of the invention illustrating the use of the flexible tail in association with a tubing connection.

FIG. 5 is a perspective view of an embodiment of the invention which includes a longitudinal slit therein to enable the holding device to be opened.

FIG. 6 is a perspective view of the construction of FIG. 5 illustrating the article holding device in opened position.

FIG. 7 is a perspective view of another embodiment of the invention which is similar to FIG. 5 with the lower end portion of the stem being omitted.

FIG. 8 is a perspective view of another embodiment of the invention.

DESCRIPTION OF THE PREFERRED EMBODIMENTS

Referring now specifically to FIGS. 1-4, the article gripping device illustrated is generally designated by the reference numeral 10 and includes an elongated tubular stem 12 which tapers gradually inwardly and downwardly from a top edge 14 to a smaller bottom end 16 with the inner and outer surfaces of the stem 12 generally paralleling each other and curving inwardly and downwardly in a smooth curve with a convex inner surface 18 and a concave outer surface 20 as best illustrated in FIG. 3. Depending from the top edge 14 of the stem 12 is an outwardly flared skirt or flange 22 which defines an acute included angle at 24 between the outer surface 20 and the interior of the outwardly inclined skirt 22.

Depending from the bottom end 16 of the stem 12 is a flexible, resilient tail 26 which tapers to a narrow terminal end 28 with the tail 26 forming an extension of the bottom end 16 of the stem 12.

The article gripping device 10 is constructed of one piece of material and, preferably, of flexible, resilient material such as rubber, plastic or the like which can be sterilized, autoclaved and constructed inexpensively to enable it to be economically disposable after use.

As illustrated in FIG. 1, the article gripping device can be used for holding an article such as a needle sheath 30 for a needle 32 mounted on syringe 34 with the needle sheath 30 being telescopically received into a major portion of the stem 12 as illustrated in broken line in FIG. 3. The depending skirt 22 is of a size to cover and protect the thumb 36 and forefinger 37 on the non-dominant hand 38 of a person holding and manipulating the syringe 34 having the needle 32 thereon by using their dominant hand thereby protecting the hand 38 as well as the thumb and fingers from accidental needlesticks thereby more effectively maintaining the integrity of the skin of the hand, thumb and fingers. The flexibility and resiliency of the article holding device 10 enables the walls of the stem 12 to be collapsed inwardly by the thumb and forefinger exerting inward pressure thereon to collapse the wall of the stem 12 into gripping engagement with the needle sheath 30 thereby securely holding and stabilizing the needle sheath.

FIG. 4 illustrates the article holding device 10 being utilized with the tail 26 wrapped around a tube 40 such as an IV tube or a male/female connection 41 or the like to more effectively hold and stabilize the tube 40 or connection 41 when some work operation is being performed on the tube 40 such as separating the male and female connection 41 or a connection which may include a sleeve telescoped into adjacent ends of the tube 40. The flexibility and resiliency of the tail 2 enables it to be spirally wrapped around the tube 40 or the connection 41 and easily gripped for securing the tube 40 and connection 41 to prevent it from slipping between the thumb and forefinger or fingers which are used to grip the tail and thus grip the tube 40 or connection 41 when loosening the connection 41.

FIGS. 5 and 6 illustrate another embodiment of the article holding device generally designated by the numeral 50 with the holding device of this invention including a tubular stem generally designated by the numeral 52 which includes an inwardly inclined upper portion 54 and a plurality of stepped cylindrical segments 56 extending vertically downwardly to the bottom end 58 of the stem 52. A downwardly and outwardly flared skirt 60 is connected to the stem 52 at the top edge 62 thereof with the stem 52 and skirt 60 being of unitary construction. The entire stem and skirt is provided with a longitudinal slit 64 extending completely through the longitudinal extent of the stem and skirt with the slit 64 including longitudinal offset portions 66 thus providing a zig-zag slit through the longitudinal dimension of the article holder 50 with the slit 64 being located at one longitudinal edge portion thereof to enable the flexible, resilient unitary member forming the article holding device 50 to be pivoted to an open position as illustrated in FIG. 6 to enable lateral assembly of an article to be held into the interior of the article holding device 50 or to enable the article holding device 50 to be opened and laterally inserted onto an article to be gripped. The bottom end 58 of the article holding device 50 is provided with a flexible, resilient tail 68 integral with the periphery of the bottom edge 58 in a manner similar to that illustrated in FIGS. 1-4.

FIG. 7 illustrates a gripping device 50' which includes the same upper end configuration as the device in FIGS. 5 and 6 and primed reference numerals are used in FIG. 7. As shown, the stem 52' is shorter than stem 52 in FIGS. 5 and 6 and includes only a single cylindrical element 56'. This form of the gripping device is especially useful in receiving and gripping a relatively short lateral port formed on an IV tube to hold the IV port while inserting a syringe needle or the like. A tail 68' may be used on the gripping device 50'.

FIG. 8 illustrates another embodiment of the invention which is in the form of a flared gripping device generally designated by reference numeral 70 that is integrally formed with a lateral port 72 on an IV tube 74. The gripping device 70 includes a generally cylindrical disc 76 having a convex surface 78 and a concave surface 80 in encircling relation to the IV port 72 to enable the thumb and forefingers to grasp the port by engaging the convex side of the gripping device 70 with the concave side facing the syringe needle to be inserted into the diaphragm 82 in the IV port thereby protecting the thumb and forefinger from needlestick or needle puncture when introducing medication to the IV tube through the IV port 72. The disc 76 is connected to the tube 74 and port 72 by a thickened or wider gripping area at 75.

The article gripping device of this invention has for its basic purposes the protection of the non-dominant hand from injury and to assist the non-dominant hand in the role it plays in various activities in which the non-dominant hand grips, holds and stabilizes a workpiece when a work operation is being performed thereon by the dominant hand or a tool or instrument held by the dominant hand. By using the article gripping device of this invention, the non-dominant nature of the non-dominant hand becomes more functional and the person performing the work operation or task that is initiated by the dominant hand becomes more aware of the existence and function of the non-dominant hand. Thus, the present invention increases the ability and role of the non-dominant hand and also shields it from injury. The article holding device may be constructed of various sizes convenient to be held by the non-dominant hand. As indicated, one major use of the invention is in the medical field and, for this purpose, three convenient sizes could be made such as a larger size for the pharmacy, a medium size for the medication room and a smaller size for personal use by the nurse. The embodiment used by a nurse may be smaller, portable, non-sterile and compact enough to be carried in the nurse's pocket or pocket protector along with scissors, clamps and other devices normally carried by a nurse. The article holding device is effectively useful for holding needle sheaths 30 as illustrated in FIGS. 1-3, a medication vial, an ampule, a tube, a tube connection and for other uses in which it is desirable to insert an article to be held longitudinally into the open upper end of the article gripping device. The embodiment of the invention illustrated in FIGS. 5-7 enables the article gripping device to be opened due to its resilient construction and placed on or receive an article to be gripped.

The gripping device can be used to hold various articles such as the ampules, vials, needle sheaths and the like and can also be used to stabilize tubing for uncapping ports or drawing from ports or injecting into ports as well as separating tubings at connections and the like. The article gripping device provides a convenient arrangement to effectively grasp, apply force, separate, maintain leverage and protect against injury in a safe and efficient manner to enable increase in the role of the non-dominant hand and to protect the non-dominant hand from injury. The device is relatively simple in construction, universal in use, safe, cost effective and disposable or reuseable depending upon the aseptic requirements. Most importantly, it reduces injury to persons engaged in various activities in which the non-dominant hand is subjected to the danger of injury.

The tapered stem in both embodiments of the invention is the key to its versatility of use since this allows various articles, objects or items to be placed into the gripping device and, depending upon the point at which the article is stopped by the tapered stem, that is where it can be gripped properly by exerting lateral inward force on the stem. The short tail on the article gripping device operates somewhat in the nature of a tourniquet and is quite effective in loosening a connection in tubing. When difficulty is encountered in loosening a tubing connection, it is conventional to employ clamps which frequently results in cracked plastic tubing due to excessive pressure from the clamp. This can be a serious matter in certain procedures such as when using a Swan-Ganz catheter which then requires either clamping off a much needed line or placing a new catheter through an introducer port and into place. The tail is a small piece of rubber which provides sufficient leverage to separate a tubing connection without damaging existing equipment and the tapered end of the tail is intentionally constructed to allow it to grip any size connection and enables careful handling near sterile connections as compared to an existing tourniquet or rubber glove which may get in the way of the procedure thus presenting a greater potential for contamination.

When used in association with an IV tube and port as illustrated in FIG. 8, the port on the IV tube is provided without any capping device and is thus free to the open air so that once touched or left open to air for any length of time it is then considered non-sterile. IV ports are used and reused with an alcohol wipe normally being used to cleanse the rubber diaphragm located in a center of the port which is held with the non-dominant hand. The article gripping device 70 provides better leverage while stabilizing the narrow IV port along the IV tubing and can be made thicker than and integral with the main shaft of the port adjacent the diaphragm end of the port or anywhere between the diaphragm end and the juncture between the port and tubing with the flared article gripping device 70 aiding against accidental contamination of the port diaphragm with the non-dominant hand thus saving time which occurs when it is necessary to recleanse the port diaphragm. In many procedures, the IV tubing is changed every 48 to 72 hours depending upon the protocol of the hospital or other facilities and, in most situations, injury to the non-dominant hand with a sterile needle is a much lower medical priority than a medical crisis which may be at hand. However, a break in skin integrity with the potential hazard it poses for infection is an increasingly serious concern of those engaged in various aspects of the medical profession. The pain and preventive measures which must be taken following a needlestick or exposure to contaminants are not only time consuming but also emotionally stressful.

The invention is adapted for various other uses including use in conjunction with a buff cap which is a single IV port plugged into an IV catheter which is directly entered into the vein and under the skin of a patient which allows the staff to have IV access to the vein for timed medications which may be hours apart or, in the case of an emergency, to enable access in seconds without bothersome tubing extending to a machine if fluids are not needed on a continuing basis. The buff cap is flushed with a solution to prevent clotting at periodic intervals and several needlesticks are required into the buff cap port thereby providing the opportunity for injury and enabling the flared gripping device 70 to effectively protect the nurse as well as the patient because of the close proximity of the buff cap to the skin. This device may also be used with valves or stopcocks incorporated into tubes or flow lines, pressure tubing of various arrangements, IV containers, blood product containers and the like. In addition to the medical field, the gripping device has substantial utility in other trades or professions where the capability of the non-dominant hand to grip a workpiece can be effectively enhanced by the gripping device. Carpenters, electricians, plumbers and various other individuals who are required to hold tools or workpieces while a work operation is being performed thereon can effectively utilize the gripping device to protect the non-dominant hand while the dominant hand is performing the work operation thereby increasing the efficiency of the work operation and protecting the non-dominant hand from injury. The gripping device is also effectively used by the elderly or handicapped who may have arthritis or other conditions which adversely affect their ability to grip small items such as medicine container caps and the like. Also, the gripping device can be effectively used as an occupational therapy device.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An article gripping device comprising an annular member of an elongated tapering configuration forming a large end and a small end, an outwardly inclined skirt on the large end of the annular member with the free end of the skirt extending toward the small end of the annular member, the length of the skirt being substantially less than the length of the annular member and defining an annular open area included between the inner surface of the skirt and the outer surface of the annular member for receiving the thumb and opposing finger of a user gripping the annular member as well as protecting the thumb and finger when the annular member is utilized to grip an article positioned in the annular member when performing a work operating on the gripped article, said annular member and skirt being of unitary construction and constructed of resilient, flexible material to enable opposed lateral forces exerted inwardly on the annular member to collapse the annular member inwardly into gripping engagement with an article being gripped, said annular member being in the form of a tapering stem extending from said large end to said small end, said large end of the stem being joined with a smaller end of the outwardly inclined skirt with the free end of the skirt being larger than the large end of the stem and extending toward the small end of the annular member, and an elongated, flexible tail connected with the small end of the annular member for wrapping around and gripping engagement with an article to be gripped when opposing lateral forces are exerted by the thumb and fingers on the external surface of the tail.

2. The structure as defined in claim 1 wherein said annular member and skirt are peripherally continuous.

3. The structure as defined in claim 1 wherein said tail is of tapered configuration and adapted to be spirally wound on the article to be gripped.

4. The structure as defined in claim 1 wherein said annular member and skirt include a radially extending longitudinal slit extending throughout the length thereof to enable the annular member and skirt to be opened to enable lateral insertion of an article or enable the gripping device to be laterally inserted onto an article to be gripped.

5. An article gripping device comprising an annular member of an elongated tapering configuration forming a large end and a small end, an outwardly inclined skirt on the large end of the annular member with the free end of the skirt extending toward the small end of the annular member, the length of the skirt being substantially less than the length of the annular member and defining an annular open area included between the inner surface of the skirt and the outer surface of the annular member for receiving the thumb and opposing finger of a user gripping the annular member as well as protecting the thumb and finger when the annular member is utilized to grip an article positioned in the annular member when performing a work operating on the gripped article, said annular member and skirt being of unitary construction and constructed of resilient, flexible material to enable opposed lateral forces exerted inwardly on the annular member to collapse the annular member inwardly into gripping engagement with an article being gripped, said annular member being in the form of a tapering stem extending from said large end to said small end, said large end of the stem being joined with a smaller end of the outwardly inclined skirt with the free end of the skirt being larger than the large end of the stem and extending toward the small end of the annular member, said annular member and skirt including a radially extending, continuous, longitudinal slit extending throughout the length of the skirt and annular member to enable the edges of the slit to be moved apart to define a longitudinally continuous opening extending from end-to-end of the annular member and skirt to enable lateral insertion of an article or enable the gripping device to be laterally inserted onto an article to be gripped.

6. The structure as defined in claim 5 wherein said longitudinal slit is of zig-zag configuration.

7. An article gripping device comprising an annular member, an outwardly inclined skirt mounted on one end of the annular member with the free end of the skirt extending toward the other end of the annular member and defining an annular space included between the inner surface of the skirt and the outer surface of the annular member with the space opening toward the free end of the skirt and the other end of the annular member for receiving the thumb and opposing finger of a user gripping the annular member as well as protecting the thumb and finger when the annular member is utilized to grip an article positioned in the annular member when performing a work operation on the gripped article, said annular member and skirt being of unitary construction and constructed of resilient, flexible material to enable opposed lateral forces exerted inwardly on the annular member to collapse the annular member inwardly into gripping engagement with an article being gripped, said annular member and skirt including a single radially extending, continuous longitudinal slit extending throughout the length of the skirt and annular member to enable the edges of the slit to be moved apart to define a longitudinally continuous opening extending from end-to-end of the annular member and skirt to enable lateral insertion of an article or enable the gripping device to be laterally inserted onto an article to be gripped.

8. The structure as defined in claim 7 together with an elongated, flexible tail connected with the other end of said annular member for wrapping around and gripping engagement with an article to be gripped when opposing lateral forces are exerted by the thumb and fingers on the external surface of the tail.

* * * * *